United States Patent [19]

Lisec

[11] Patent Number: 4,781,586
[45] Date of Patent: Nov. 1, 1988

[54] ARTICULATOR FOR SIMULATING MOVEMENTS OF THE MANDIBLE

[76] Inventor: Bernhard Lisec, Kupferzeile 25, A-4810 Gmunden, Austria

[21] Appl. No.: 9,466

[22] Filed: Feb. 2, 1987

[30] Foreign Application Priority Data

Feb. 10, 1986 [AT] Austria .................................. 312/86

[51] Int. Cl.[4] .................................................. A61C 11/00
[52] U.S. Cl. ............................................ 433/57; 433/61
[58] Field of Search ........................ 433/57, 58, 61, 62, 433/63, 65, 66

[56] References Cited

U.S. PATENT DOCUMENTS

| | | | |
|---|---|---|---|
| 3,159,915 | 12/1964 | Beu et al. | 433/57 |
| 3,590,487 | 7/1971 | Guichet | 433/62 |
| 4,245,987 | 1/1981 | Bertoldi | 433/61 |
| 4,365,955 | 12/1982 | Tradowsky | 433/57 |

*Primary Examiner*—Samuel Scott
*Assistant Examiner*—Noah Kamen
*Attorney, Agent, or Firm*—Kurt Kelman

[57] ABSTRACT

In a dental articulator for simulating movements of a mandible relative to an upper jaw, comprising an upper part (2, 4) adapted to carry an upper jaw model (7), a lower part (1) adapted to carry a lower jaw model (8), and a hinge (13, 13) connecting said upper and lower parts, the hinge defining an axis (A-B) extending substantially horizontally in a plane extending substantially perpendicularly to the upper and lower parts for articulating said upper part with respect to the lower part about the hinge axis: the invention provides two pins (18) displaceably mounted in a first laterally extending slot (22) in the upper part (4), the pins extending downwardly from the upper part and being adapted to be fixed in said first slot, a constraining bar (19) fixed to said lower part (1), the constraining bar having a constraining edge in front of said plane and facing rearwardly towards said hinge axis, and the constraining edge being engageable with said pins (18) and spaced from the axis a distance corresponding to the radius of said pins, and two stops (20) displaceably mounted in a second laterally extending slot (21) in said lower part (1), the stops being adapted to be fixed in said second slot and extending upwardly from the lower part for engagement with said pins (18) to cooperate therewith for controlling horizontal components of a simulated chewing movement of said upper and lower articulator parts relative to each other.

11 Claims, 4 Drawing Sheets

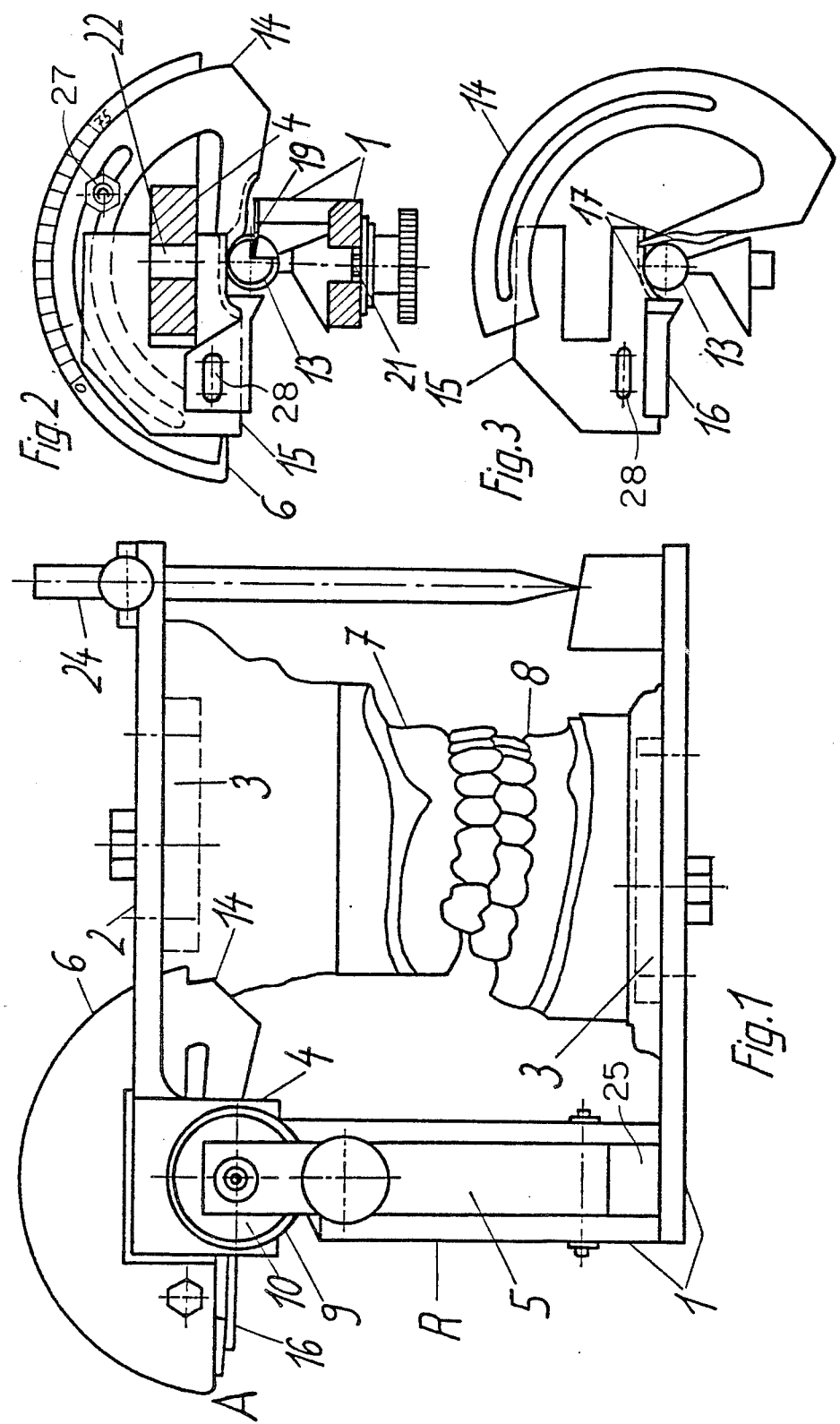

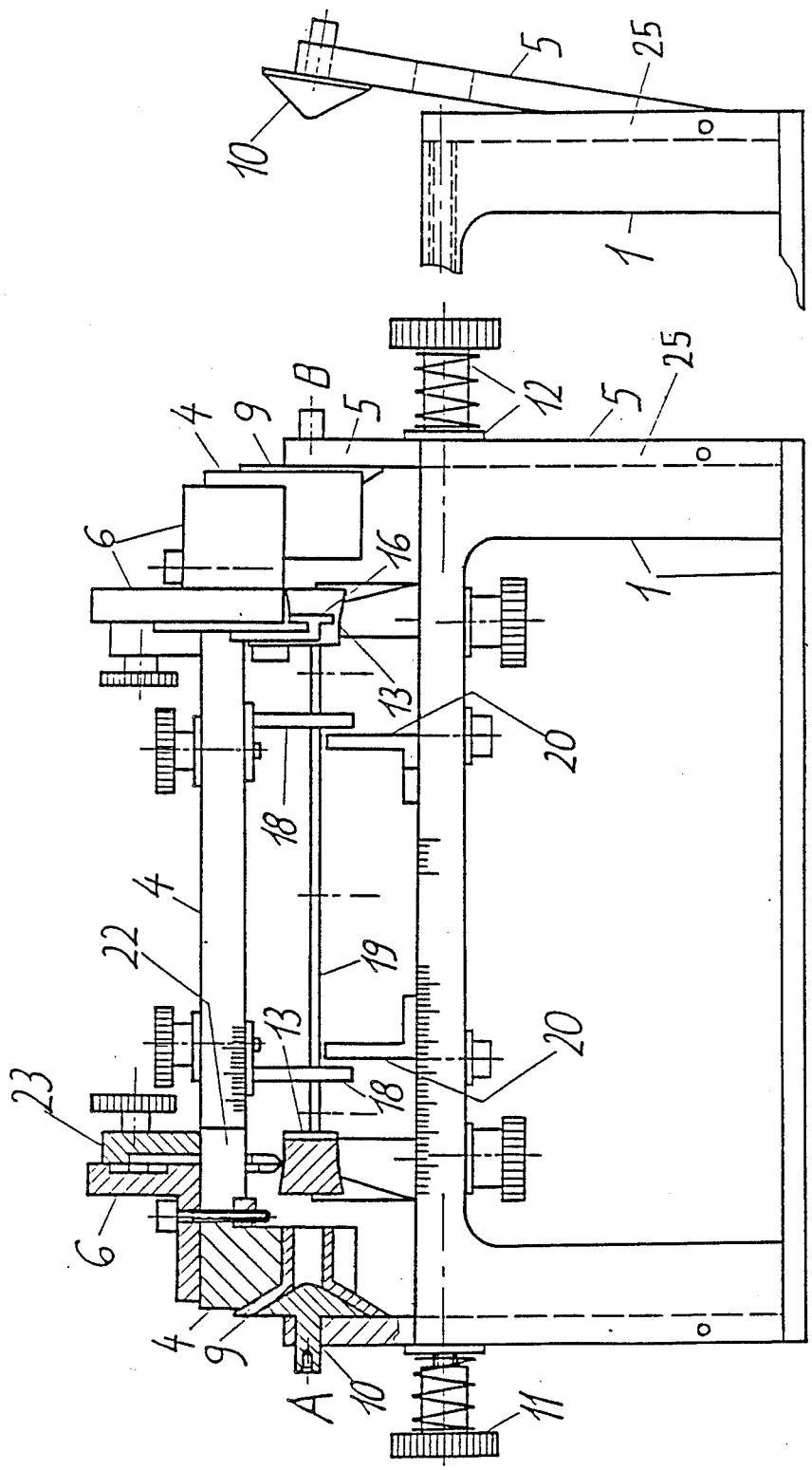

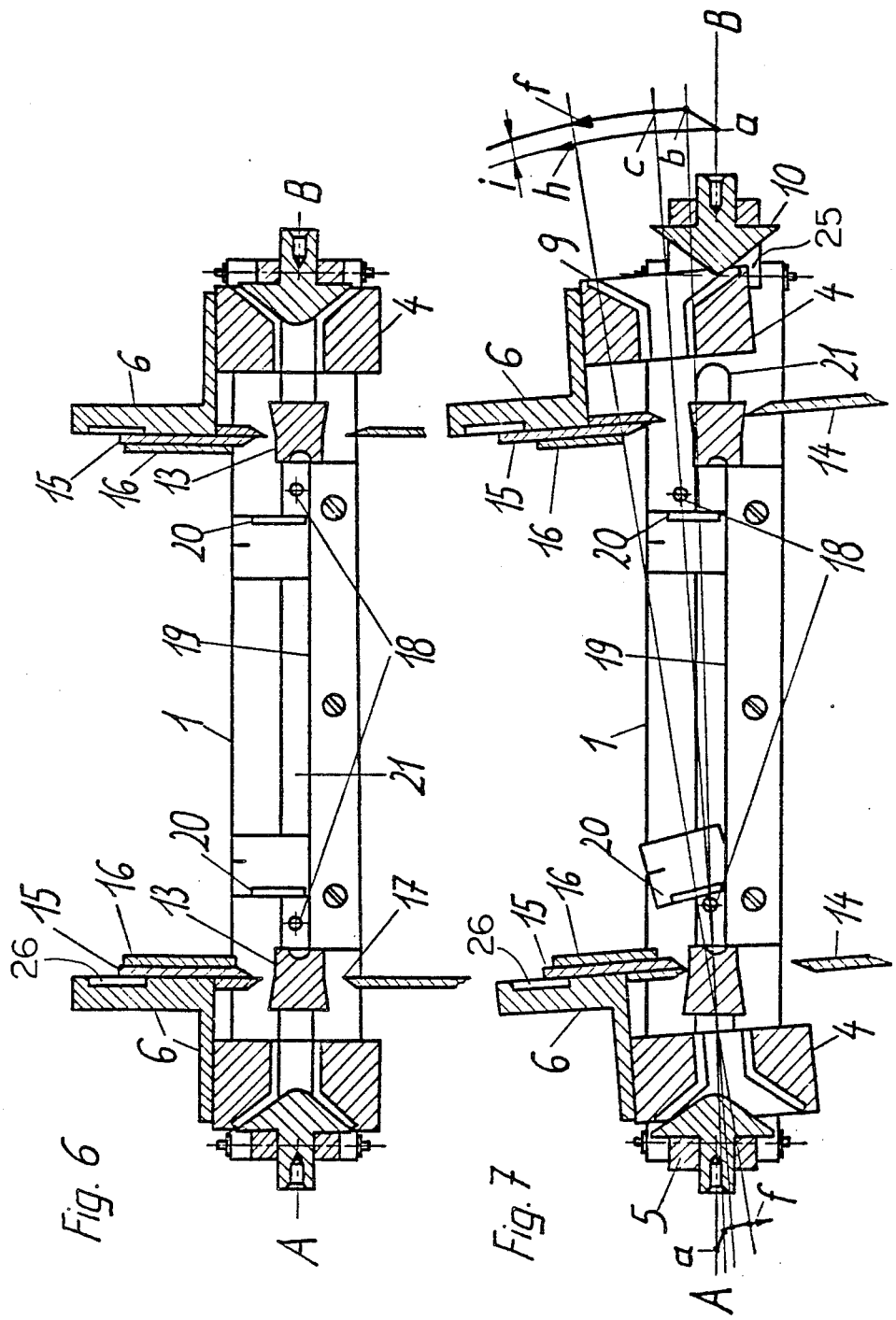

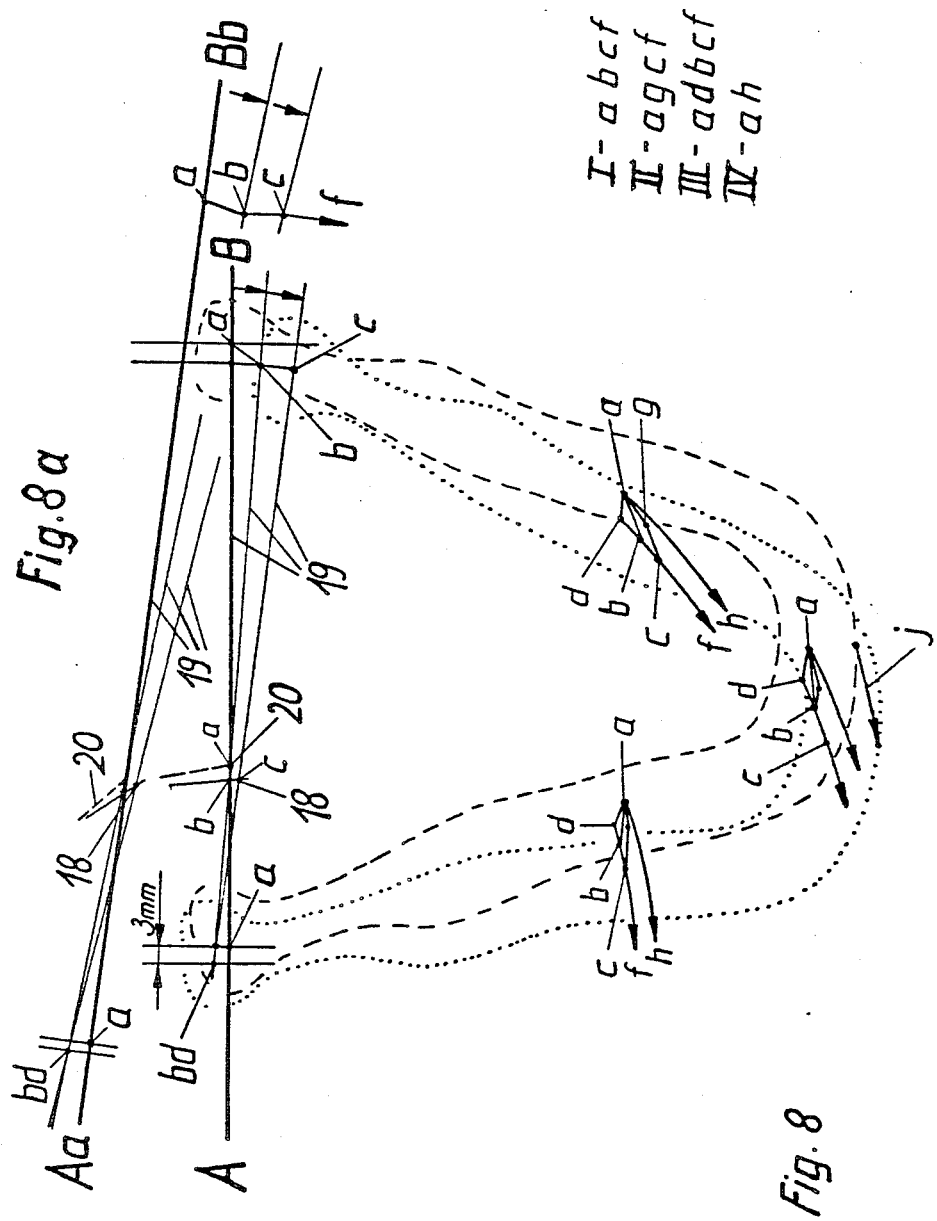

ARTICULATOR FOR SIMULATING MOVEMENTS OF THE MANDIBLE

FIELD OF THE INVENTION

This invention relates to an articulator for simulating movements of the mandible.

DESCRIPTION OF THE PRIOR ART

Articulators are dental devices in which models of toothless jaws or of jaws set with teeth are mounted in such a manner that the relative position of the jaw models agrees with the position of the jaws in the mouth of the patient. The simplest type of articulator is a simple hinge or a mechanical interlock; in that case an exact simulation can be achieved only when the teeth are closed, i.e., in the occlusion position. If it is required to simulate also the open, prebite and lateral bite positions whereas a high accuracy is not necessary, it is usual to use so-called semi-adjustable articulators, which have hinges consisting of ball pins or other pins sliding on surfaces or in slots. Said surfaces or slots are radially adjustable with respect to the axis of the articulator so that the forward and downward inclination of the path of the jaw joint can be reproduced. The distance between the joints is determined in accordance with average anatomical values. Face arches are used to ensure that the models are mounted relative to the axis of the articulator in the required relation to the axis of the jaw joint. The inclination of the path defined by the joint is adjusted in accordance with average values or in accordance with recorded bites. Recorded bites are impressions taken simultaneously in the mouth in suitable impression-taking material from the upper and lower jaws, whether they are toothless or set with teeth. Said recorded bites represent the right-hand, left-hand and advanced position of the mandible relative to the upper jaw.

With the aid of such recorded bites the paths defined by the articulator hinge can be adjusted when the models have been inserted into the impressions corresponding to the recorded bites when the articulator has been opened. Previously, the models had to be mounted in the articulator exactly in the correct position relative to the axis.

Such articulators can be used when there is an adequate incisor overbite and an incisor guidance has been provided and the molars separate quickly during lateral movements of the mandible. If an incisor guidance cannot be established, an incorrect simulation of the chewing movements would have the result that humps of the molars would engage each other prematurely in the region in which the strongest chewing force is exerted. Corresponding artificial teeth would be unstable and might be prematurely destroyed and give rise to pathologic changes of the chewing apparatus. In order to avoid a premature engagement of humps of molars and to ensure that all teeth will uniformly slide on each other during the chewing action, T.M.J. Stuart et al have developed a device which is known as a pantograph and can be used to record the motions of the mandible on 6 recording plates, which are mounted on the patient. Thereafter said movements can be transferred to fully adjustable articulators. In said articulators the distances between the jaw joints can be individually adjusted and the articulators are provided with concentric locking means which in case of need fix the axis of the articulator in such a position that only a pure hinge motion can be performed from the occlusion position. The joints have sliding surfaces, which are in sliding contact with ball heads and have a profile which substantially agrees to the curved paths described by the individual chewing movements. When the profile of the chewing movements is simulated in hardenable plastic in accordance with the records taken from the patient, said pits of the joint will agree to an accuracy of a few hundredths of a millimeter with all mandible movements which can be performed by the patient.

Said devices are known to have the disadvantage that while the dental technician in making a denture can find a large number of paths on the surfaces of the joint, said paths need not agree with the preferred paths of movement of the patient. The records taken by Gibbs from chewing patients by means of the replicator system indicate that certain paths are preferred and that they have a highly characteristic timing. The difficulty resides in that during a lateral chewing movement of the mandible, when one joint head is sliding forwardly and downwardly along the path defined by the joint, the second joint head does not rotate about its axis with most patients but owing to a lateral displacement of the mandible may perform an outward movement to an extent which varies greatly with different patients and may amount to as much as 3 mm, and the mandible may also move rearwardly and upwardly or rearwardly and downwardly approximately to the same extent. That movement is much quicker and will be terminated before the joint head on the opposite side has completed its movement of about 10 mm.

An exact observation shows that in that part of the movement both joint heads move approximately along an arc of a circle having an imaginary center that is disposed behind and between the joints. The distance of said center from the rotating joint head will depend on the extent of the lateral and rearward movement and on the ration of the velocities of the two joint heads along their paths. For this reason each point of the mandible describes during a lateral movement a defined curved path relative to the upper jaw and said path will not merge into an arc of a circle until the rotating joint head has reached its most laterally outward and rearmost stop position in the joint on the working side. That arc of a circle is centered in the joint.

The movements described hereinbefore are performed in the reverse sequence during a chewing action. To facilitate the understanding they have been described here in the sequence in which they are performed for practical reasons in the articulator. To facilitate the manipulation, the upper jaw part of the articulator is moved toward the mandible portion.

SUMMARY OF THE INVENTION

It is an object of the invention to provide an articulator having two hinge joints which comprise only a few replaceable parts and are adjustable in such a manner that it permits a simulation to an accuracy which approximates that which can be achieved with individually shaped joints. A constraining mechanism is provided which during a lateral movement of the lower part of the articulator relative to the upper part will positively constrain the lower part to move relative to the upper part along an adjustable curved path in a movement which corresponds to the chewing movement of the natural jaw.

A new and advantageous feature of the present invention resides in that the combination of the novel constraining mechanism and of the novel design of the sliding surfaces of the joints results in a correct curved chewing path for each main direction of movement from the occlusion position and this is ensured by the provision of individually adjustable segments which conform to the curves which are specific to a given patient. It is preferred to provide recorded bites taken in the mouth and in that case the position of the hinge axis of the mandible of the patient and the distance between his or her jaw joints need no longer agree exactly with the position of the hinge axis and distance between the joints of the articulator.

BRIEF DESCRIPTION OF THE DRAWINGS

FIG. 1 is a side elevation showing the articulator.

FIG. 2 shows the mechanical jaw joint viewed from the center of the articulator.

FIG. 3 illustrates the adjustment of the paths defined by the joint.

FIG. 4 is a rear view showing the articulator.

FIG. 5 shows a rocker 5, which has been pivotally moved laterally out of the guide groove of the lower part 1 and is provided with a centering cone 10.

FIG. 6 is a horizontal sectional view showing the entire joint of the articulator and taken on the hinge axis A-B viewed from above, when the hinge is in a centered position.

FIG. 7 is a sectional view like FIG. 6 and shows the hinge when the upper and lower parts of the articulator have been laterally displaced relative to each other as by a lateral chewing movement of the mandible to the right.

FIG. 8 is a diagrammatic view illustrating the novel control mechanism.

DESCRIPTION OF THE PREFERRED EMBODIMENT

The invention will now be described more in detail with reference to the drawings.

In FIG. 1, a lower part 1 of the articulator is shown, also an upper part-retaining arm 2, model-mounting plates 3, a crosspiece 4 of the upper part, upper jaw and mandible models 7 and 8, respectively, and a backing pin 24. These parts are designed as is usual in known dental articulators.

The control mechanism provided in accordance with the invention comprises a constraining bar 19, which is fixed to the lower part 1 of the articulator and tapers to a thin constraining edge, which in a view from the rear lies on the same level as the hinge axis of the articulator (see FIGS. 2 and 4). In a top plan view as shown in FIGS. 6 and 7, that edge is parallel to the axis and is spaced in front of it by the radius of the pins 18. The pins 18 (FIGS. 4, 6, 7) are mounted in the upper part of the articulator in the slot 22 and are laterally displaceable therein and can be fixed by screws in such a position that the axes of the pins 18 intersect the axis of the articulator at right angles in the closed position of the articulator. Right-hand and left-hand stops 20 (FIGS. 4, 6, 7, 8,) are laterally displaceably mounted in the transverse slot 21 of the lower part 1 of the articulator so that said stops can be fixed in position after a pivotal movement about their axes (FIGS. 7, 8,). In accordance with the invention the lower part 1 is constrained to perform a progressive three-dimensional lateral movement by the rockers 5, which are shown in FIGS. 4, 5, 6, 7 and are provided with centering cones 10, spring bias adjusting screws 11 and springs 12 for cooperation of cones 10 with conical sockets 9 of the upper part 4 of the articulator. An auxiliary pivot is pushed through the bore of said sockets when the articulator hinge is to be programmed or checked with the aid of a plot made by a pantograph. FIGS. 6, 8 and show the articulator in a closed position before a chewing movement. In that position, both cones 10 are urged into the conical sockets 9 by means of the two rockers 5 (FIGS. 4, 5), which are biased by the springs 12 (FIG. 4), which are prestressed by the adjusting screws 11. Those positions of the two rockers 5 are defined by their guidance in grooves 25 provided in the lower part 1 (FIG. 4) on both sides. The axis A-B shown in FIGS. 4, 6, 7 and 8 corresponds to the imaginary hinge axis for the mandible. When said axis has been determined on the patient by means of a pantograph or by another known method and with the aid of a face arch, the jaw models are correspondingly mounted in the articulator so that the hinge axis of the mandible agrees with the hinge axis A-B of the articulator. The contour of the mandible in that position is indicated by dotted lines in FIG. 8 and corresponds to the occlusion, in which the humps of the teeth of both jaws have a maximum interlock. Points a in FIG. 8 designate apices of humps of left-hand and right-hand lower molars and a point on the lower incisors. The following steps are taken to adjust the hinge of the articulator so that it matches the chewing movements of a given patient:

When the screws 11 associated with the springs 12 have been losened, the rockers 5 provided with the centering cones 10 are pivotally moved laterlly out of the lower part 1 of the articulator. The recorded bite simulating a lateral movement of the mandible is then introduced between the models. In FIGS. 7, 8 and, this is the bite corresponding to a lateral movement to the right. The contour of a mandible in that position is shown by dotted lines in FIGS. 8. In the resulting relative position of the upper and lower parts of the articulator, the axes intersect, as is shown in FIGS. 7, 8. That pin 18 of the upper part 4 which corresponds to that end of the hinge is so adjusted with reference to the corresponding intersection that the peripheral surface of the pin 18 contacts the edge of the constraining bar 19. When the pin 18 has been fixed in position, the stop 20 of the lower part 1 is fixed on contact with the pin 18, as is shown in FIG. 7. In the same adjusting sequence the right hand path-defining segment 15, which serves to control the rearward movement of the roll-like right-hand joint head 13, and the path-defining segment 16, which serves as a stop limiting that movement, are moved until the controlling edges of the segments 15 and 16 contact that rolllike joint head and the segments 15 and 16 are then fixed in postion. During a movement to the right, the mandible moves also in a forward and downward direction. In order to simulate also the latter movement, the path-defining segment 14 on the left of the articulator is adjusted in the same sequence until the camming edge of that segment 14 contacts the roll-like left-hand joint head 13 (FIG. 7). After a corresponding adjustment with respect to the recorded movement to the left, the hinge of the articulator has been completely programmed for the registered lateral movements.

To move the articulator in accordance with the lateral chewing movement of a given patient, in the drawings in accordance with a movement to the right, the rockers 5 are operated to move the centering cones 10 into the conical sockets 9 (FIG. 6) and the compression spring 12 on the right-hand or working side of the hinge is highly prestressed by means of the adjusting screw 11. The spring 12 on the opposite, left-hand side is prestressed by the associated adjusting screw to a much smaller degree, which is just sufficient to hold by means of the rocker 5 and the centering cone 10 the upper part of the articulator in its centered position (FIGS. 1, 4, 6). When pressure in the direction of the arrows (FIG. 7) is applied to the upper part of the articulator in order to simulate a chewing movement to the right, the right-hand cone 10 will cause the conical socket 9 to cant and slide down so that the upper part of the articulator is urged against the cone on the other side where the cone and the associated rocker yield laterally because the compression spring 12 is under a lower initial stress. Until the pin 18 engages the stop 20 and the joint head 13 engages the segment 16, the pin 18 slides along the edge of the guide bar 19 (FIGS. 7, 8) so that a movement is performed which for the points indicated in FIGS. 7, 8 corresponds to the movement along path I from a to b. As that movement is continued the pin 18 moving along the sliding surface of the stop 20 departs from the control edge 19 so that the movement along path I from b via c to f is controlled. As is particularly apparent from FIG. 8 and, the provision of the axially adjustable stop 20 in accordance with the invention ensures that when the rotating joint head has engaged the segment 16 and the stop 20 has been axially adjusted in accordance with the registrate, a continued movement will cause an arcuate path to be projected for each point of the mandible (in FIG. 8, path I from b toward f) and the center of said path will always be identical to the center of rotation of the mandible after the rotating jaw head has reached the most laterally outward and most rearward position. This will be the case even if the jaw models are not mounted in the articulator in correct position relative to the axis and the distance between the joints is not the same as the distance between the joints of the patient.

To permit an adequate three-dimensional lateral movement of the mandible, centering cones are used which are 20 mm in diameter and have an included angle up to 45°.

The lateral movement of the mandible exceeds 1 mm only with very few patients.

Owing to the novel pivotal mounting provided in accordance with the invention for centering cones in dental articulators, a reliable and highly stable locking in a centered position is ensured.

That arrangement affords the great advantage that the force of the spring 12 will cause the articulator to return to the central position of the hinge automatically and exactly to the centered position after a simulated chewing movement. Compared to the known fully adjustable articulators, much time and work is saved because the central interlock need not be loosened and fixed before and after each simulated chewing movement.

The novel design of the parts of the mechanical articulator hinge which serve to simulate the movement in accordance with the proper curves and with the proper inclinations of the movements of the natural joint heads on their sliding surfaces in the joint is shown in FIGS. 2 and 3. The hinge comprises first path-defining segments 14, which are pivotally movable about the axis of the upper part of the articulator and serve to guide the forward movements of the mandible model. Said segments 14 comprise a camming edge 17, which has a curved shape that corresponds to the shape of the natural jaw joint. The segment 14 is fitted into an arcuate groove 26 of the segment carrier 6 and is fixed in said groove 26 by a screw 27 when the path has been adjusted to the proper inclination. The second path-defining segment 15 defines the path for the rearward movements of the joint head 13 and is displaceable forwardly and rearwardly in a slot 28 of the upper part 4 of the articulator and is fixed to the segment carrier 6 by a screw together with the third path-defining segment 16, which serves as a stop that limits the rearward movement. The segment carriers shown in FIGS. 1, 2, 4, 6 and 7 are secured to the crosspiece 4 of the upper part of the articulator in such a manner that the distance between said carriers can be adjusted in dependence on the distance between the jaw joints of the patient if this is desired or required.

FIGS. 4 and 7 indicate the novel design of the joint heads 13 provided in accordance with the invention. Each of them consists of an approximately cylindrical pivot portion and of a screw-threaded base that is laterally adjustably mounted in the slot 21 (FIGS. 2, 6 and 7) of the lower part 1 of the articulator and can be fixed in such a position that the central peripheral portion, which has a radius of 4.5 mm, will contact the edges of the path-defining segments 14, 15 (FIG. 2) always at the same point during pivotal movements of the articulator. The axis of the roll-like joint heads agrees with the axis A-B of the articulator (FIGS. 4 and 6). As is conventional in fully adjustable articulators the distance between the joint heads 13 can be adjusted by moving them along the slot 21 in the lower part 1 of the articulator. In accordance with the present invention the roll-like joint heads 13 (FIGS. 4, 6 and 7) have a changing radius so that their surface configuration matches the natural chewing movements of the patient. The upper part of the articulator is correspondingly raised or lowered in accordance with the recorded bite during three-dimensional lateral movements of the upper part of the articulator as the camming edges 17 of the path-defining segments 14 and 15 slide on said peripheral surfaces of the heads 13. A large number of curved paths can be adjusted with the aid of a small number of joint heads which are kept in stock and have a profile which rises or falls from the circularly cylindrical portion, and which can be used in the right-hand or left-hand joint of the articulator or may be inserted in the lower part of the articulator after a rotation through 180°. Owing to the novel design of the path-defining segments. The movements of the mandible of a patient can be simulated even when the models are not mounted in the articulator exactly in the correct position relative to the axes and the joints.

FIG. 8 is a diagrammatic top plan view showing the development of curved paths for chewing movements in an articulator. Paths I and II may be obtained in the articulator in accordance with the invention. Paths II, III and IV are obtained in known articulators. A comparison of these paths reveals the difference between the movements of the points a toward point f during a lateral movement of the mandible to the right.

In FIG. 8, dotted lines indicate the position assumed by the mandible when the left-hand jaw head has slid forwardly by 10 mm, the mandible has peformed a three-dimensional lateral movement by 3 mm and the rotating joint head has moved rearwardly by 3 mm. Path I will be obtained when the hinge of the articulator is provided with the control device according to the invention and has been adjusted so that the rotating joint head reaches its most laterally outward and most rearward position when one joint head has slid forwardly by 5 mm.

Path II will be described by the points a when the rotating joint head is constrained by the straining means to reach its end position only after a forward sliding movement by 10 mm.

Path III is obtained in all fully adjustable articulators known thus far when the most latererly outward and rearward position is immediately assumed by the rotating joint head before the sliding movement on the other side begins.

Path IV will be obtained if the three-dimensional lateral movement of the mandible is not simulated.

From FIG. 8 it is apparent that owing to the new constraining mechanism it is no longer necessary to move the models in the articulator exactly in the correct position relative to the axis. The position of the axis Aa-Bb of the articulator differs greatly from the position of the hinge axis A-B of the mandible.

Orthodontic treatments of children to correct the shape of their jaws and the position of their teeth will be facilitated by the use of the articulator in accordance with the invention as shown in FIG. 4 regarding the chewing function and its evaluation.

I claim:

1. In a dental articulator for simulating movements of a mandible relative to an upper jaw, comprising an upper part (2, 4) adapted to carry an upper jaw model (7), a lower part (1) adapted to carry a lower jaw model (8), and a hinge (13, 13) connecting said upper and lower parts, the hinge defining an axis (A-B) extending substantially horizontally in a plane extending substantially perpendicularly to the upper and lower parts for articulating said upper part with respect to the lower part about the hinge axis: the improvement comprising
    (a) two pins (18) displaceably mounted in a first laterally extending slot (22) in the upper part (4), the pins extending downwardly from the upper part and being adapted to be fixed in said first slot,
    (b) a constraining bar (19) fixed to said lower part (1), the constraining bar having a constraining edge in front of said plane and facing rearwardly towards said hinge axis, and the constraining edge being engageable with said pins (18) and spaced from the axis a distance corresponding to the radius of said pins, and
    (c) two stops (2) displaceably mounted in a second laterally extending slot (21) in said lower part (1), the stops being adapted to be fixed in said second slot and extending upwardly from the lower part for engagement with said pins (18) to cooperate therewith for controlling horizontal components of a simulated chewing movement of said upper and lower articulator parts relative to each other.

2. The improvement set forth in claim 1, wherein each of said stops (20) is angularly adjustable to constrain said pins (18) engaged with said stops to perform horizontal movements along desired curved paths even when said models (7, 8) are mounted in said articulator parts (2, 1) in a position which does not correspond to the position of the upper jaw end of the mandible of a patient relative to the jaw joints.

3. The improvement set forth in claim 1, wherein
    (a) the upper part (4) has two laterally open and laterally outwardly flaring conical sockets (9) centered on the hinge axis (A-B), and further comprising
    (b) two generally vertical rockers (5) pivoted to said lower part (1) for lateral movement in said plane, the rockers fitting into respective laterally outwardly open, vertically extending guide grooves (25) at respective ends of the lower part (1),
    (c) a respective centering cone (10) carried at an upper end of each one of the rockers and pivotally movable thereby into a respective one of the sockets (9) for centering the cones on said hinge axis (A-B) and for permitting said upper part (4) to perform an angular movement about said axis,
    (d) a respective compression spring (12) bearing on each rocker (5) and laterally inwardly biasing the rocker into a respective one of the guide grooves (25) until the cone (10) engages the socket (9) in the upper part, and
    (e) a respective adjusting screw (11) for prestressing said compression springs (12).

4. The improvement of claim 1, adapted for simulating chewing movements of the mandible in three main directions including a rearward direction, wherein the hinge comprises
    (a) two roll-like joint heads (13, 13) spaced from each other along said axis (A-B), and
    (b) a respective first, second and third segment (14, 15, 16) associated with each joint head and respectively defining movement paths extending in respective ones of said directions upon constraining engagement with a respective one of said joint heads, the segments being independently pivotal about said axis and each third segment (16) serving as an adjustable stop for limiting the movement of the joint head engaged thereby in said rearward direction.

5. The improvement of claim 4, further comprising a respective carrier (6) for said three segments, the carriers being secured to the upper articulator part (4) and the segments being plate-shaped.

6. The improvement of claim 5, wherein one of said chewing movement path directions is a forward and downward direction defined by the plate-shaped first segments (14) having an arcuate periphery, each carrier defines an arcuate groove (26) conforming to the arcuate segment periphery and guiding the same during pivotal movement about a center of the arcuate periphery in said axis (A-B), the first segments (14) have curved camming edges in sliding contact with the joint heads and define arcuate slots concentric with the arcuate segment periphery and arcuate groove (26), and further comprising a respective screw (27) extending through the arcuate slot in each first segment (14) for fixing the same in desired pivotal positions.

7. The improvement of claim 5, wherein the first and second segments (14 and 15) have curved camming edges (17) in sliding contact with the joint heads, one of said chewing movement path directions is a forward and backward direction defined by the second segments (15), and the second segments (15) define a respective rectilinear slot (28) for displacing each second segment forwardly and rearwardly on the carrier (6) with respect to the joint head (13).

8. The improvement of claim 7, wherein the camming edges (17) of the first and second segments (14, 15) are juxtaposed and chamfered to define a common sharp edge, the common sharp edge being in sliding contact with a peripheral surface of a respective one of the roll-like joint heads (13).

9. The improvement of claim 5, wherein the plate-shaped segments (14, 15, 16) each have arcuate peripheral portions centered on said axis (A-B) and camming edges (17) having a circular portion in sliding contact with the roll-like joint heads (13, 13), each carrier defines an arcuate groove (26) conforming to the arcuate segment peripheral portion and guiding the segments during pivotal movement about the axis (A-B), and further comprising means (27) for fixing the segments in desired pivotal positions.

10. The improvement of claim 9, wherein said lower part (1) defines a second laterally extending slot (21), and the roll-like joint heads (13, 13) have a base slidably mounted for displacement along said axis (A-B) and adapted to be fixed in the second laterally extending slot, and each joint head having a cylindrical portion of uniform radius and an adjoining frusto-conical portion of varying radius, the camming edges (17) in sliding contact with the cylindrical and frusto-conical portions of the joint heads controlling the directions of the simulated chewing movements in laterally displacement positions of the joint heads.

11. The improvement of claim 10, wherein each joint head has a central portion having a radius of about 4.5 mm.

* * * * *